United States Patent [19]

Amundson

[11] 4,033,355
[45] July 5, 1977

[54] ELECTRODE LEAD ASSEMBLY FOR IMPLANTABLE DEVICES AND METHOD OF PREPARING SAME

[75] Inventor: David Charles Amundson, Minneapolis, Minn.

[73] Assignee: Cardiac Pacemakers, Inc., St. Paul, Minn.

[22] Filed: Nov. 28, 1975

[21] Appl. No.: 635,909

[52] U.S. Cl. ............................ 128/404; 128/419 P; 174/120 SC
[51] Int. Cl.² .................................................. A61N 1/00
[58] Field of Search ............... 128/404, 418, 419 P; 174/120 SC

[56] References Cited
UNITED STATES PATENTS

| | | | |
|---|---|---|---|
| 2,377,153 | 5/1945 | Hunter et al. | 174/120 SC |
| 3,284,562 | 11/1966 | Stebleton | 128/418 |
| 3,474,791 | 10/1969 | Benton | 128/418 |
| 3,924,639 | 12/1975 | Hess | 128/418 |

FOREIGN PATENTS OR APPLICATIONS

| | | | |
|---|---|---|---|
| 84,040 | 8/1971 | Germany | 128/419 P |
| 311,643 | 10/1971 | U.S.S.R. | 128/418 |

*Primary Examiner*—William E. Kamm
*Attorney, Agent, or Firm*—Orrin M. Haugen

[57] ABSTRACT

An implantable electrode lead assembly for coupling an electrical stimulator pulse generator to an internal organ and a method for preparing such an assembly, the electrode lead assembly including a coiled conductor wound in the form of a helix about a central axis. An electrical conductor is encapsulated within a coaxially disposed flexible cylindrical sleeve, with the sleeve including separate inner and outer tubular elements. The inner tubular element is fabricated from a semiconductive silicone rubber having a resistivity of less than about 130 ohm-cm., and with the outer tubular element comprising an electrically insulative silicone rubber, with both tubular elements having the property of expanding upon exposure to certain solvents or other mediums. The preparation operations utilize the expansion characteristic to form a unitary lead assembly. The arrangement is such that in the finished lead assembly upon fracture of the electrical conductor means, the inner semi-conductive tubular element acts as a back-up conductor which will provide a conductive path so as to continue delivering reasonably normal or reasonably effective stimulator pulses from the pulse generator through the lead assembly and to the conductive electrode tip or tips.

6 Claims, 4 Drawing Figures

ELECTRODE LEAD ASSEMBLY FOR IMPLANTABLE DEVICES AND METHOD OF PREPARING SAME

BACKGROUND OF THE INVENTION

The present invention relates generally to a lead assembly for the electrodes of an implantable electrical pulse generator delivering stimulating pulses to an internal organ, and more specifically to such a lead assembly which retains a conductor means therewithin, and is provided with a conductive encapsulating tube which will provide electrical continuity and continued conductivity for the assembly in the event of rupture or severance of the conductors. More specifically, the conductive encapsulating tubular element provides both electrical back-up and a compressive force to grip the conductor means therewithin and reduce the extent of migration of the free ends of fractured wires.

In the design of implantable lead assemblies for delivering stimulating electrical pulses from a pulse generator to an internal organ, such as, for example, a cardiac pacer device or the like, the lead assembly must be sufficiently flexible so as to accommodate flexure at a rate, for example, the normal 72 beats per minute of the human heart. In the past, various types and combinations of conductor means have been employed, and in particular a coiled lead wound in the form of a helix has been widely used. These leads are normally metallic conductors, and have been fabricated from stainless steel such as MT 35 stainless. This material is sufficiently flexible so as to permit its use in implanted lead assemblies.

As has been indicated, and recognized in the art, implantable leads must be sufficiently flexible so as to not interfere with the normal function of delicate systems within the patient. At the same time, these leads must be sufficiently durable so as to withstand substantially constant flexural motion, while, at the same time, withstanding such flexural motion at localized zones or areas along the extent of the lead. Upon occasion, the conductor system may become separated due to fracture, and when this occurs in the assembly of the present invention, conductivity continues by virtue of a conductive sleeve which is arranged to compressively grip the coiled conductors. The structure of the present invention provides an electrically conductive path which is designed so to not be adversely affected by those same forces which tend to either damage or destroy the continuity of the metallic conductor.

SUMMARY OF THE INVENTION

Briefly, in accordance with the present invention, the lead assembly utilizes a core in the form of a coiled conductor or conductors which are wound in the form of a helix, and wherein a semi-conducting silicone rubber is arranged so as to compressively grip the outer diameter of the conductive helix. The semi-conductive tubular element is, in turn, encapsulated within an outer insulative tubular element, with the outer tube, in turn, compressively gripping the outer diameter of the inner tubular element. This arrangement provides for a highly flexible lead assembly which is durable and yet provides for continued functional operation even upon the occurrence of a break, such as a fracture or other undesireable separation of the coiled lead.

Therefore, it is the primary object of the present invention to provide an improved implantable lead assembly and method of preparation thereof wherein the assembly is arranged for coupling a stimulating pulse generator to an internal organ, with the lead assembly including means at one end for coupling to the output of a pulse generator, and with conductive electrodes or tips being disposed at the distal or free end of the lead.

It is a further object of the present invention to provide an improved implantable electrode lead assembly for coupling the output of an electrical pulse generator to an internal organ wherein the lead assembly includes a coiled electrical conductor wound about a central axis to form a helix, and wherein the coiled conductor is compressively gripped within a semi-conductive silicone rubber tube, with the semi-conductive tube being, in turn, compressively gripped within a second or outer insulative tubular element.

It is yet a further object of the present invention to provide an improved implantable electrode lead assembly and method of preparing same wherein the lead assembly is arranged for coupling the output of an electrical pulse generator to a conductive electrode tip wherein conductors are provided in the form of a coiled helix, with the helix being encapsulated within inner and outer tubular elements, the inner tubular element being in the form of a semi-conductive silicon rubber which is treated to expand for reception of the conductor, and thereafter to shrink and return to its original configuration, the inner tubular element compressively gripping outer diameter of the coiled conductor helix, and with the semi-conductive tubular element being, in turn, being similarly encapsulated and compressively gripped within an insulative outer tubular element.

These and other objects of the present invention will become apparent to those skilled in the art upon a study of the following specification, appended claims, and the accompanying drawing.

DESCRIPTION OF THE PREFERRED EMBODIMENT

Figure 1:
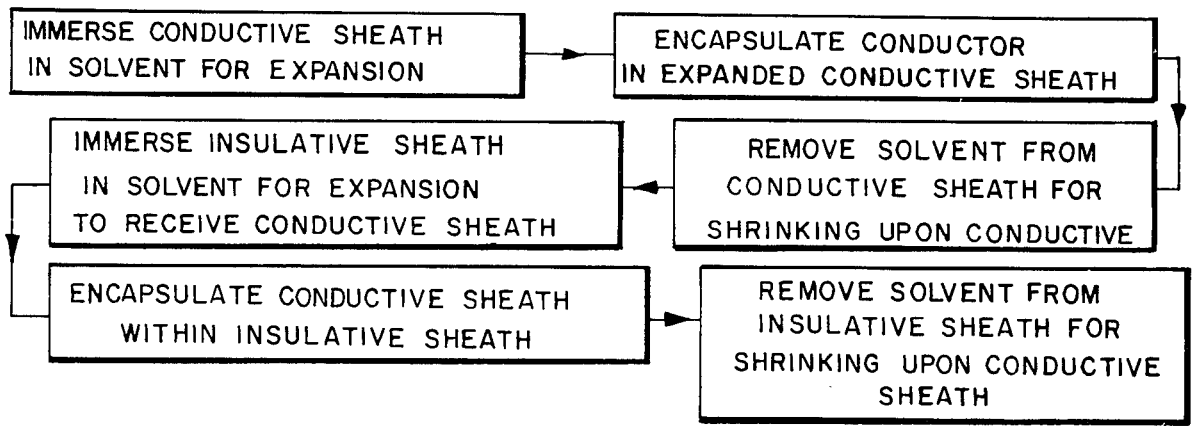
FIG. 1 is a block diagram of a method employed to prepare the improved implantable electrode lead assemblies of the present invention.
Figure 2:
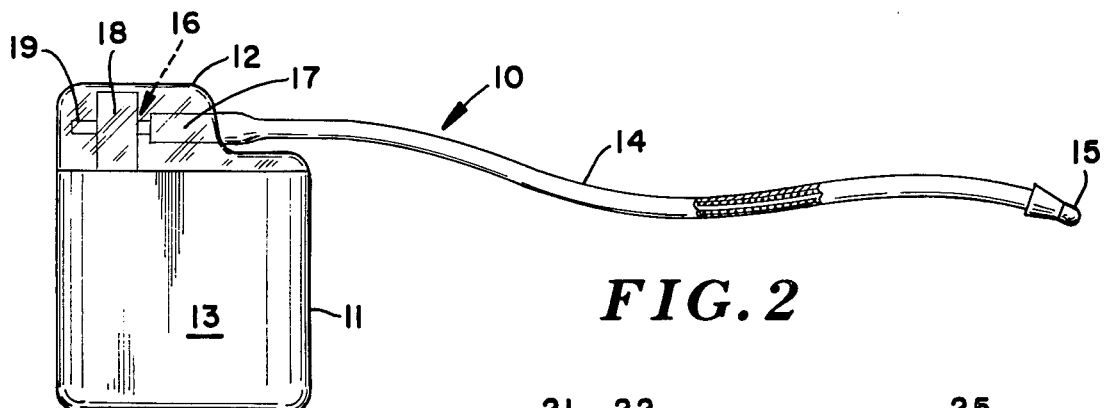
FIG. 2 is a plan elevational view of a typical pulse generator having the implantable electrode lead assembly of the present invention operatively secured thereto, with a portion of the lead assembly being broken away.

In accordance with the preferred embodiment of the present invention, and with particular attention being directed to FIG. 2 of the drawing, the cardiac pacer assembly generally designated 10 includes a pulse generator enclosed within casing 11, having a lead attachment head shown at 12. The pulse generator is shown at 13, it being understood, of course, that pulse generator 13 is enclosed generally within casing 11. Lead assembly 14 is shown coupled to the pulse generator, with lead assembly 14 extending from coupling zone or station 12 to the conductive electrode tip shown at 15. Conductive tip 15 is, of course, exposed and is generally in physical contact with the tissue to be stimulated, such as the heart muscle in the case of the cardiac pacer device.

The arrangement of the device illustrated in FIG. 2 is that of an unipolar cardiac pacer, and the assembly may be in the form of that assembly disclosed and claimed in U.S. Pat. No. 3,822,707. The circuitry for the pulse generator 13 may be in the form of that circuitry disclosed in co-pending application Ser. No. 515,463, filed Oct. 17, 1974 and now abandoned, and entitled "CARDIAC PACER CIRCUIT", Jon A. Anderson and Richard W. Kramp, which application is assigned to the same assignee as the present application.

In order to couple the lead to the pulse generator, a coupling arrangement is illustrated generally at 16, with the arrangement including a sleeve or the like 17 in head 12 for receiving the proximal end of the lead, and with the conductor per se being clampingly engaged by set screw 18 prior to final implantation. Preferably, the entire head 12 which is spaced from casing 11 is fabricated from a clear and transparent material so as to permit a visual sighting of the conductor portion 19 as it extends through the area from the set screw.

It will be appreciated, of course, that bipolar leads may be prepared utilizing the features of the present invention which provide for continued conductivity between portions of the individual conductor elements either of which may become separated due to fracture of the conductor. For purposes of comprehending the concept, however, a unipolar device is disclosed for simplicity.

Figure 3:
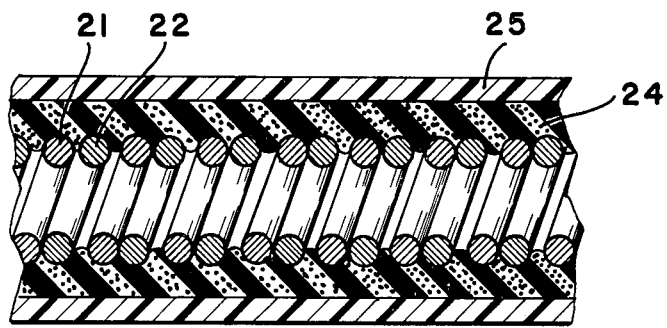
FIG. 3 is a detail sectional view of a segment of the lead assembly, with FIG. 3 being shown on a slightly enlarged scale, and illustrating the detail of the lead.
Figure 4:
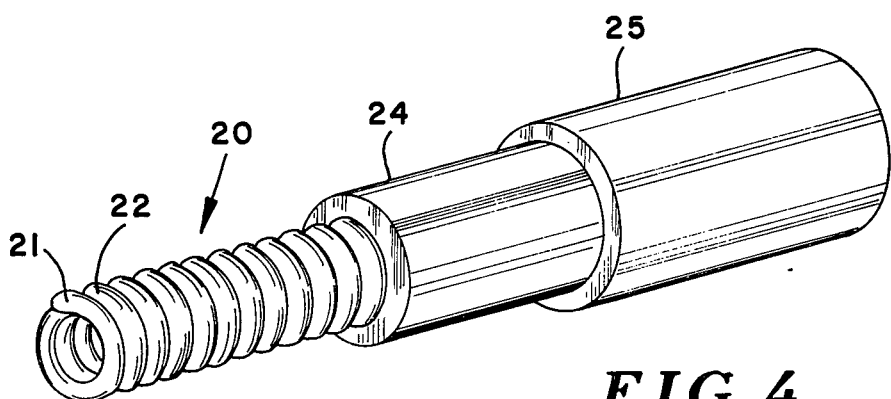
FIG. 4 is a detail perspective view of the electrode lead assembly of the present invention, and illustrating the coiled conductor along with the tubular elements encapsulating the conductor, with the conductor and the tubular elements being partially broken away, and with FIG. 4 also being shown on a slightly enlarged scale.

Attention is now directed to FIGS. 3 and 4 of the drawing wherein the details of the lead assembly are illustrated. Specifically, as illustrated in FIG. 3, the conductor system generally designated 20 includes a pair of parallel spans 21 and 22, each of which is arranged in a helical pattern about a common axis. Also, the coiled conductors have a generally uniform outer diameter, as is apparent in FIGS. 3 and 4. A pair of coaxially disposed tubular elements 24 and 25 enclose the coiled conductors 21 and 22 as will be more fully explained hereinafter.

In the embodiment illustrated, the first tubular element 24 is disposed about the outer periphery of the conductor, with tubular element 24 compressively gripping the outer diameter. Preferably, tubular element 24 is prepared from semi-conducting silicone rubber, and preferably has an electrical resistivity of less than about 130 ohm-cm. and even more preferably less than about 100 ohm-cm. The outer tubular element 25 is, as indicated, electrically insulating, and also compressively grips the outer periphery of the inner tubular element 24. It is desirable that the outer tubular element compressively grip the inner tubular element so as to improve the flexural characteristics of the assembly, without introducing frictional contact between the mutually mating surfaces of the inner and outer tubular elements.

MATERIALS OF CONSTRUCTION

As has been indicated, the material of construction for the conductors is preferably stainless steel type MT 35. This material is substantially inert to body fluids, and also posesses mechanical properties which include the requisite flexural characteristics and tensile strength. Resistance to fatigue is a further consideration. In the embodiment illustrated, a pair of coiled conductors are provided, it being appreciated, or course, that a single coiled conductor may be useful in certain installations, and in certain other installations or applications more than two such coils could be found useful.

Typically, for cardiac pacer applications, the conductor normally has a diameter of 0.006 inches, and is coiled as to form a helix having a diameter of approximately 0.035 inches. For most purposes, the helix will have a pitch of about 0.014 inches.

While stainless steel has been recommended, for certain other applications, platinum or platinum-iridium alloys may be required, although for most applications stainless steel has been found reasonably useful and applicable.

For the preparation of the tubular element 24, an electrically semi-conductive silicone rubber is utilized. Such materials are, of course, commercially available, with one such material found useful being that certain silicone rubber sold under the code designation Silastic S-2086 by Dow Corning Corporation of Midland, Michigan. This material, as molded, has an electrical resistivity of approximately 60 ohm-cm., but when cured for 24 hours at a temperature of approximately 250° C. the resistivity drops to approximately 8 ohm-cm.

The outer tubular element 25, as previously indicated, is essentially insulative in nature. Any silicone rubber may be employed, with one such rubber being medical grade Silastic Tubing and available from Dow Corning Corporation of Midland, Michigan, and approved for use as an implantable device or component.

As previously indicated, the electrode tips such as is illustrated at 15 are typically prepared from stainless steel of type MT 35. These tips are, of course, exposed directly to the tissue being stimulated and, as such, comprise the active element delivering the stimulator pulse to the patient from the pulse generator.

PROCEDURE

In order to prepare the assembly, the coiled conductor is placed within the interior of a semi-conductive tubular element such as the element 24, with the tubular element having an internal diameter less than the outer diameter of the conductor helix. For a conductor helix having an outer diameter of, for example, 0.035 inches, the tubular element should have an internal diameter of approximately 0.034 inches. The tubular element is immersed in a material which causes expansion of the tubing, such as, for example, a fluorinated hydrocarbon such as Freon, preferably a Freon which remains in liquid state under ordinary ambient conditions. As an alternate, xylene or toluene may be employed for expanding the tubing. In this connection, therefore, the tubing is immersed in the Freon or other selected material until expansion occurs, and sufficient expansion for receiving the coiled helix therewithin. Following introduction of the conductor in the form of a coiled helix therewithin, the combination is baked until the solvent is driven off, with a baking for a period of six hours at 250° C. normally being sufficient.

The semi-conductive tubing, as indicated, has a post-cure inner diameter of about 0.034 inches, with a wall thickness sufficient to provide an outer diameter of about 0.060 inches. The outer tubing is selected so as to provide an interference fit with the outer periphery of the inner tubing. In this connection, with an inner tubing having an outer diameter of about 0.060 inches, the outer tubing will have an inner diameter of approximately 0.060 inches as well, with the outer tubing being likewise immersed in Freon, xylene, or toluene so as to expand the tubing to receive the inner tubing therewithin. Following such treatment, the structure is again baked or post-cured at a temperature of approximately 250° C. for a period of about 6 hours. Such a post-cure or baking cycle is sufficient to remove any residual solvent which may remain, and provide a system which is acceptable as an implantable device.

ELECTRICAL CONSIDERATIONS

As has been indicated, the resitivity of the inner tubing is selected so as to be between about 8 ohm-cm. and 130 ohm-cm. Typically, in a stimulator such as a cardiac pacer device, the electrical load is normally in the area of approximately 500 ohms. For stimulation of a muscle such as the heart, 1 to 2 milliamperes are required. With a pulse generator having an output of 5 volts for stimulating the heart muscle, it will be appreciated that an impedence of up to 5,000 ohms could reasonably be handled. Typically, the system will be designed so as to provide power of the order of 10 milliamps for the muscle stimulation, however, as indicated, 1 to 2 milliamperes will normally be sufficient to stimulate the heart muscle.

In the coiled assembly, the tubular element 24 compressively grips the conductors 21 and 22 therewithin. In view of the compressive gripping forces, it has been ascertained that, for most purposes, any fracture or break in the conductor would not normally place or position the fractured ends at a distance greater than about 1 millimeter, one from the other. Therefore, in order to increase the resistance to an overall magnitude of less than 5,000 ohms, a resistivity of less than about 130 ohm-cm. will be required. The spreading resistance of the system when confronted with a conductor separation of about 1 millimeter will accommodate the arrangement when the resistivity is below about 130 ohm-cm. in this embodiment. Generally, a resistivity range of between about 10 ohm-cm. and 100 ohm-cm. is highly workable. Therefore, a system is provided which retains the mechanical properties of flexibility and durability, without sacrificing of the electrical properties. As indicated above, the forces which normally damage or destroy the metallic conductors do not adversely affect the conductive path provided by the semi- conductor rubber member.

GENERAL COMMENTS

The present invention provides an implantable electrode lead assembly which is self-healing in the event of a break occuring in the conductor element per se. The system is one which permits a patient time, upon occurence of the fracture, to seek medical aid in the form of a replacement of the damaged lead. When applied to a cardiac pacer, the patient will, in most instances, have sufficient time to seek and obtain medical aid and replacement of the lead.

I claim:
1. In an implantable electrode lead assembly for coupling an electrical stimulator pulse generator to an electrode tip means in contact with an internal organ to be stimulated, said electrode lead assembly comprising:
   a. conductor means encapsulated generally coaxially within a flexible cylindrical sleeve means and with said conductor means and said sleeve extending continuously between said pulse generator and said electrode tip means, said conductor means defining a conductive path from said pulse generator to said electrode tip means;
   b. said conductor means including a coiled electrical conductor would generally helically about a central axis and having a generally uniform outer diameter;
   c. said flexible cylindrical sleeve means comprising first and second coaxially disposed tubular elements enclosing said coiled conductor means and encapsulating said conductor means therewithin, with the inner diameter of said first tubular element being less than the outer diameter of said coiled conductor and compressively gripping the outer diameter of said conductor and with the inner diameter of said second tubular element being less than the outer diameter of said first tubular element and compressively gripping the outer diameter of said first tubular element;
   d. said first tubular element comprising a semi-conductive silicone rubber having a resistivity of below about 130 ohm-cm., with said second tubular element comprising an electrically insulating silicone rubber.
2. The implantable electrode lead assembly as defined in claim 1 being particularly characterized in that said first tubular element has a resistivity of below about 100 ohm-cm.
3. The implantable electrode lead assembly as defined in claim 1 being particularly characterized in that said conductors are fabricated from stainless steel.
4. The implantable electrode lead assembly as defined in claim 1 being particularly characterized in that said conductors are a pair of parallelly disposed strands of coiled metal.
5. The implantable electrode lead assembly as defined in claim 4 being particularly characterized in that said conductors have a diameter of approximately 0.006 inches, and are coiled to form a helix of approximately 0.035 inches diameter, with a pitch of approximately 0.014 inches, and with said first tubular element having a wall thickness of approximately 0.025 inches.
6. The method of encapsulating a coiled electrical conductor within an insulating sleeve for preparation of an implantation electrode lead assembly for coupling an electrical stimulator pulse generator to an electrode tip means in contact with an internal organ to be stimulated, said method comprising:
   a. selecting a first tubular element of semi-conductive silicone rubber having a resistivity of below about 130 ohm-cm., with said first tubular element having a normal internal diameter which is less than the external diameter of the coiled electrical conductor to be encapsulated;
   b. immersing said first tubular element in a solvent for expanding said tubular element until the internal diameter thereof exceeds the external diameter of said coiled electrical conductor, and inserting said coiled electrical conductor into said tubular element while expanded;

c. removing the solvent from said first tubular element for compression thereof;
d. selecting a second tubular element, said second tubular element being an insulative silicone rubber having a normal internal diameter less than the outer diameter of said first tubular element;
e. immersing said second tubular element into a solvent for the purpose of expanding said second tubular element until the internal diameter thereof exceeds the outer diameter of said first tubular element, and inserting said first tubular element into said second tubular element while said second tubular element remains expanded; and
f. removing solvent from said second tubular element so as to cause said second tubular element to return to its normal dimentional condition, thereby compressively retaining said first tubular element and coiled electrical conductor therewithin.

* * * * *

UNITED STATES PATENT OFFICE
CERTIFICATE OF CORRECTION

PATENT NO. : 4,033,355
DATED : July 5, 1977
INVENTOR(S) : David Charles Amundson It is certified that error appears in the above-identified patent and that said Letters Patent are hereby corrected as shown below:

Column 2, line 26, "silicon" should read -- silicone --.
Line 30, after "gripping" insert -- the --.

Column 5, line 57, "semi-conductor" should read -- semi-conductive --.

Column 6, line 14, "would" should read -- wound --.

Signed and Sealed this

Fourth Day of October 1977

[SEAL]

Attest:

RUTH C. MASON
*Attesting Officer*

LUTRELLE F. PARKER
*Acting Commissioner of Patents and Trademarks*